United States Patent

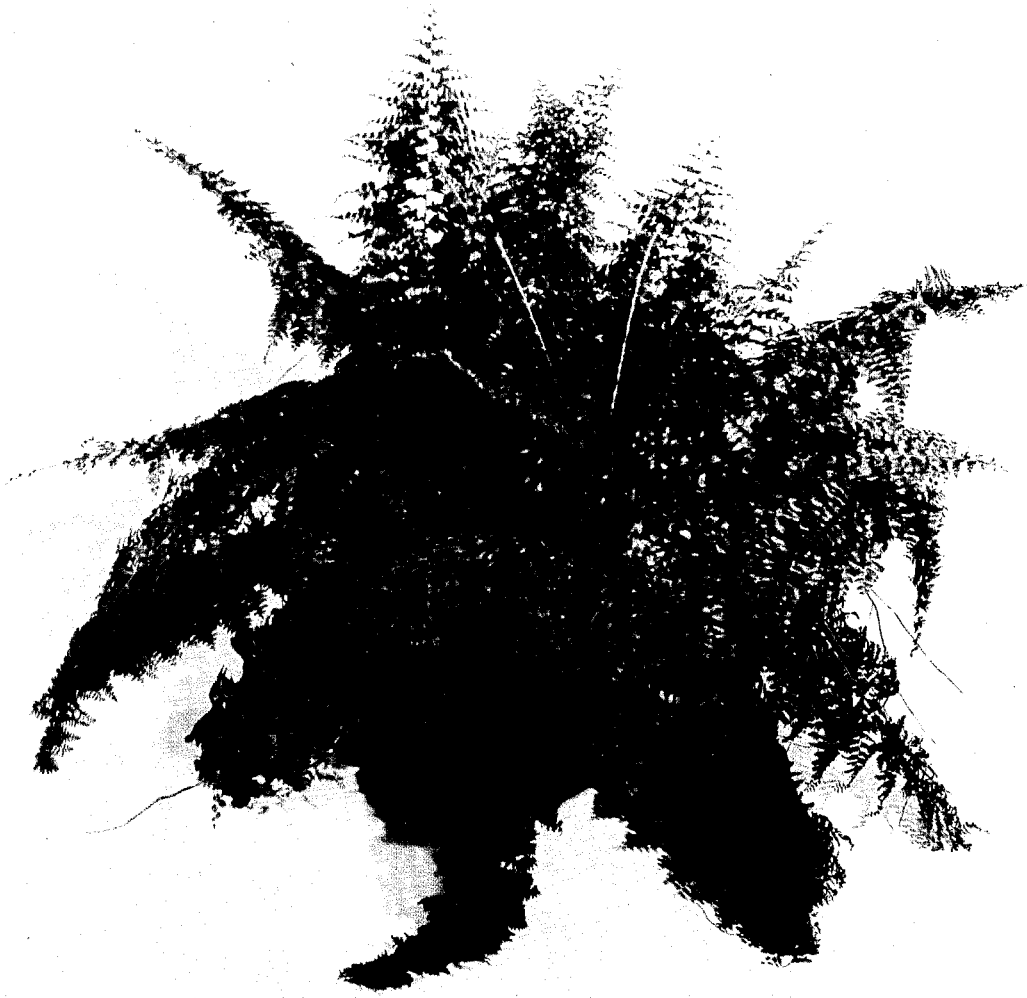

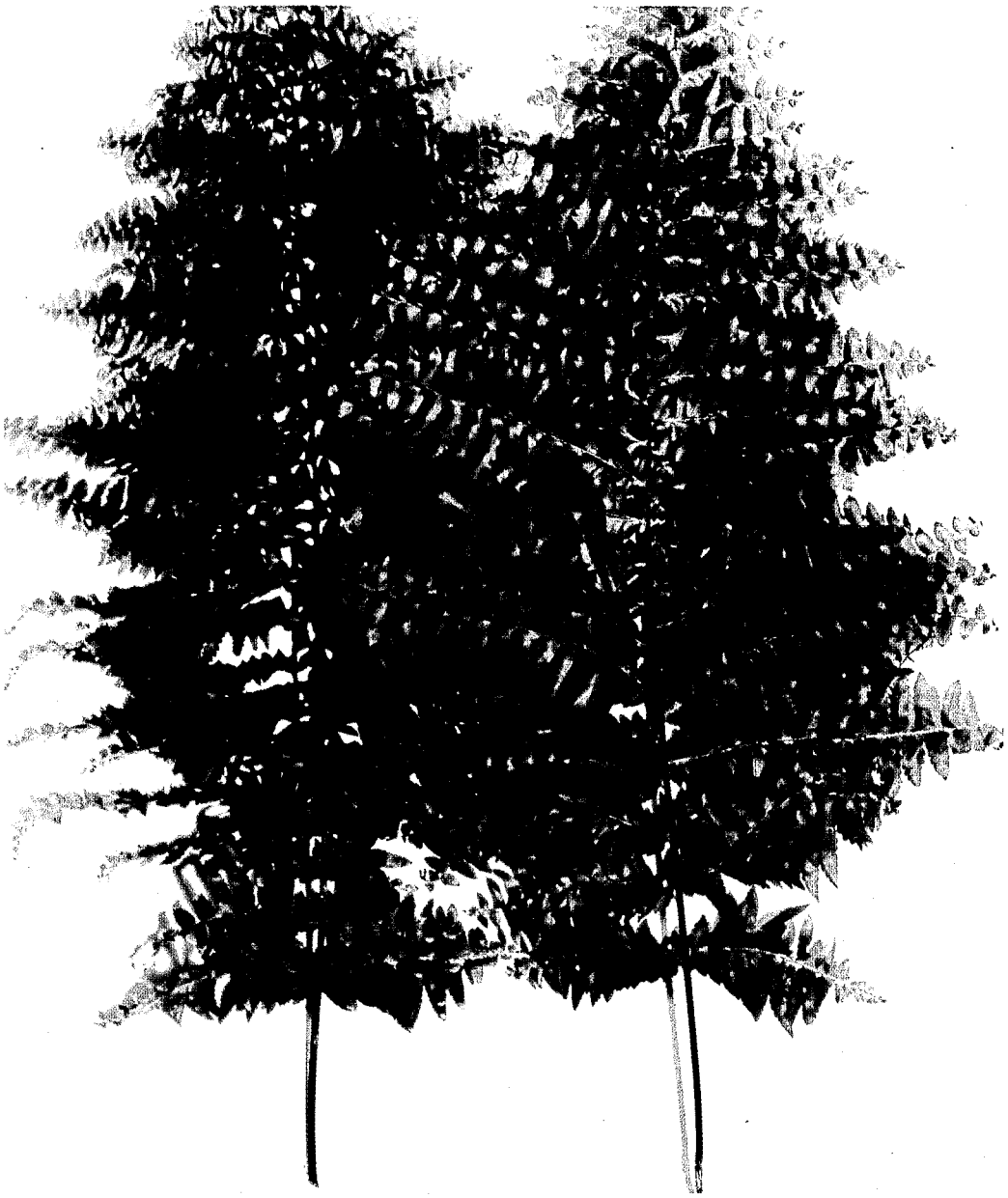

Plant Pat. 3,936

Patented July 6, 1976

3,936

PLANT OF THE FERN FAMILY

Howard G. McAllister, 1100 NW. 75th Ave., Plantation, Fla. 33313

Filed Aug. 14, 1975, Ser. No. 604,637

Int. Cl.[2] A01H 5/00

U.S. Cl. Plt.—88 1 Claim

ABSTRACT OF THE DISCLOSURE

A new and distinct plant variety of the fern family has a growth habit which provides specimens having robust appearing compound bipinnate fronds that grow in a compact rosette arrangement with a notable absence of sori. In comparison to the fronds of the "Curly Boston," the fronds are faster maturing, have a generally longer and wider appearance at maturity, and have a rachis with an abaxial surface color at its proximal end which extends further distally from the rachis and on the rachis of the "Curly Boston" and is also dominated by red and/or reddish brown hues.

The invention relates to a new and distinct plant variety of the fern (Polypodiaceae) family and which has been named the *Nephrolepis exaltata* "McAllister" by the inventor.

Plant varieties of the fern family commonly appear on the marketplace and many varieties have an unknown origin but which are nevertheless endowed with characteristics that provide greater or lesser appeal to the general purchasing public. One of the more popular varieties of the fern family is the so-called "Curly Boston" variety of the *exaltata* species. Specimens of this variety have compound pinnate fronds that grow in a fairly compact rosette arrangement and which are endowed with numerous clusters of sporangia and these sori have been frequently mistakenly considered by the unenlightened purchasing public to be clusters of insect eggs. As is the case with the "Curly Boston" variety, most varieties of the fern family have a sporophyte generation that is well endowed with sori that tend to darken in color and become more noticeable to the purchasing public as the fronds mature in age. The natural reluctance of the purchasing public to acquire plant life that is seemingly infested with insect-producing eggs is understandable and one of the objectives of the invention has been to develop a plant variety of the fern family which has an absence of sori in the frond structure. The objective of the invention has been fully realized as will be evident from the following detailed disclosure.

Specimens of the new and distinct plant variety of the fern family are characterized by compound bipinnate fronds that have a notable absence of sori and which in comparison to the fronds of the "Curly Boston" variety have a more robust appearance and more compact rosette arrangement. In comparison, they are also faster maturing and generally longer and wider in appearance at maturity than those of the "Curly Boston" variety. Apart from this, the rachis of the new variety has an abaxial surface color at its proximal end that extends further distally on the rachis when compared to the color extension on specimens of the "Curly Boston" variety and this color on the abaxial surface is characteristically dominated by red and/or reddish brown hues.

The new variety appeared as a vegetative mutation on a plant specimen of the *Nephrolepis exaltata* "Curly Boston" variety which was under cultivation in a nursery at Fort Lauderdale, Fla., and since the initial discovery of the new variety, has been asexually reproduced by the inventor at the Fort Lauderdale nursery by the propagation of stem cuttings taken from the original plant specimen. Through successive propagations, it has been ascertained that plants of the new variety may be distinguished from those of its parent variety and from other related varieties known to the inventor by a growth habit which provides specimens that have robust appearing, compound, bipinnate fronds that grow in a compact rosette arrangement with a notable absence of sori, the fronds, in comparison to those of the "Curly Boston" variety being faster maturing, generally longer and wider appearing at maturity, and provided with a rachis with an abaxial surface color at its proximal end that is dominated by red and/or reddish brown hues and extends further distally on the rachis than that of the "Curly Boston" variety.

The accompanying drawing serves, by color photographic means, to illustrate the new variety and wherein one color photograph shows a specimen of the new variety which has been grown under nursery conditions in a plastic container, and the other color photograph shows abaxial and adaxial surfaces respectively of a pair of fronds removed from the specimen shown in the other color photograph.

The following is a detailed description of the new plant variety with colors and hues, unless otherwise clearly indicated by the text, being named in accord with the ISCC–NBS Method of Designing Colors (U.S. Dept. of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md.

*Plant Description*

I. Name: *Nephrolepis exaltata* "McAllister."

II. Parentage: A vegetative mutation from *Nephrolepis exaltata* "Curly Boston."

III. Classification:
- A. Botanic—
  1. Family: Polypodiaceae (fern family).
  2. Genus: *Nephrolepis.*
  3. Species: *exaltata.*
- B. Commercial—Foliage plant.

IV. Sporophyte generation (common reference):
- A. Form: Terrestrial, herbaceous, shade loving rosette of erect young and arching to dropping mature fronds.
- B. Stems: (1) General—Rhizomatous and stoloniferous with advantitious root system. (2) Stolons—(a) General: Semisucculent and herbaceous with prolific branching, and becoming dry and brittle with age. (b) Texture: Scabrous with cespitose hairs at apexes of primary and secondary stolons and elsewhere having sparse to moderate coverage with elongated, membranous hairs that expand toward the insertion and are commonly between 2 mm. and 5 mm. in length. (c) Shape: Generally cylindrical. (d) Size: (i) Diameter—Usually between 0.2 mm. and 2 mm. (ii) Length—Indeterminate. (e) Color: Commonly light greenish yellow (near 10 Y 8/6) (near 10 Y 8/8), moderate greenish yellow (near 10 Y 8/6) (near 10 Y 8/8) (7.5 Y 7/6) (10 Y 7/6) (near 10 Y 7/8), strong greenish yellow (near 10 Y 7/8) (near 10 Y 8/8) (near 10 Y 7/10), brilliant greenish yellow (near 10 Y 8/8), light yellow green (2.5 GY 8/6) (near 5 GY 8/6), moderate yellow green (near 2.5 GY 6/6) (2.5 GY 7/6) (5 GY 6/6) (5 GY 7/6), strong yellow green (2.5 GY 7/8) (5 GY 6/8) (5 GY 7/8) (5 GY 7/10) (near 7.5 GY 6/8), and/or brilliant yellow green (near 5 GY 8/8) during early maturity.

C. Fronds: (1) General—Exstipulate, compound and foliaceous with circinate vernation and a notable absence of sori and with a rachis bearing a compact arrangement of pinnae. (2) Arrangement—Rosette. (3) Shape—(a) General: Lanceolate. (b) Frond tips: Acuminate to acute. (c) Frond bases: Acute to rounded. (4) Size—(a) Length (including stipe): usually between 40 cm. and 85 cm. at full maturity. (b) Width (maximum): Usually between 15 cm. and 40 cm. at full maturity. (5) Stipe—(a) General: Herbaceous and fleshy at early maturity and becoming dry and brittle with age. (b) Texture: Villose with the hairs being elongated membranous and expanding toward insertion, and with moderate concentration at basal insertion and sparse concentration at mergence with rachis. (c) Shape: Generally cylindrical with a lateral expansion at insertion and an adaxial surface depression or groove which becomes most prominent at mergence with rachis. (d) Size: (i) Length—Usually between 3.5 cm. and 12 cm. when measured between insertion and basally located pinna emergence at full maturity. (ii) Diameter—Usually between 1.5 mm. and 3.0 mm. intermediate insertion and basally located pinna emergence at full maturity. (e) Color: (i) General—Abaxial surface color dominated by red and/or reddish brown hues at maturity. (ii) Abaxial surface—Commonly blackish red (near 2.5 R 2/2) (near 5 R 2/2), dark grayish red (near 2.5 R 2/2) (near 5 R 2/2) (2.5 R 3/2) (5 R 3/2), very dark red (2.5 R 2/2) (5 R 2/2), dark red (near 2.5 R 3/4) (5 R 3/4) (near 5 R 3/6), dark grayish reddish brown (7.5 R 2/2) (10 R 2/1) (10 R 2/2), grayish reddish brown (near 7.5 R 3/2) (10 R 3/2), and/or moderate reddish brown (7.5 R 3/4) (10 R 3/4) (near 7.5 R 3/6) (near 10 R 3/6) (2.5 YR 3/4) at maturity. (iii) Adaxial surface—Commonly dark grayish brown (7.5 YR 2/1) and/or dark grayish yellowish brown (10 YR 2/1) adjacent insertion and merging distally with moderate yellow green (near 2.5 GY 5/4) (2.5 GY 5/6) (2.5 GY 6/6), dark greenish yellow (10 Y 6/6) and/or light olive (near 10 Y 5/4) (10 Y 5/6) at maturity. (6) Rachis—(a) General: Herbaceous and generally fleshy and flexible during early maturity and hardening with age. (b) Texture: Thin cespitose hairs during early maturity and with age becoming less matted, the distal portion of abaxial surface approaching glabrous with sparse concentration of hairs upon aging. (c) Shape: Generally cylindrical with axially extending adaxial surface depression or groove merging with that of stipe. (d) Size: (i) Length (between apex and basal pinna emergence)—Usually between 39 cm. and 75 cm. at full maturity. (ii) Diameter (intermediate apex and basal pinna emergence)—Usually between 0.75 mm. and 2.0 mm. at full maturity. (e) Color: (i) General—Distal end surface color dominated by yellow green hues and proximal end abaxial surface color dominated by red and/or reddish brown hues that extend distally to mergence, generally intermediate the proximal and distal ends, with distal end surface color. (ii) Apexes—Commonly moderate yellow green (near 2.5 GY 5/6) (2.5 GY 6/6) (5 GY 5/6) (near 5 GY 6/4) (5 GY 6/6) (5 GY 7/6) (near 7.5 GY 6/6) and/or strong yellow green (2.5 GY 6/8) (2.5 GY 7/8) (near 5 GY 6/8) (5 GY 7/8) (near 5 GY 7/10) (near 7.5 GY 7/8). (iii) Abaxial surface—Usually blackish red (near 2.5 R 2/2) (near 5 R 2/2), dark grayish red (near 2.5 R 2/2) (near 5 R 2/2 (2.5 R 3/2) (5 R 3/2), very dark red (near 2.5 R 2/2) (near 5 R 2/2), dark red (2.5 R 3/4) (5 R 3/4) (near 5 R 3/6), dark grayish reddish brown (7.5 R 2/2) (10 R 2/2), grayish reddish brown (7.5 R 3/2) (10 R 3/2) and/or moderate reddish brown (7.5 R 3/4) (10 R 3/4) at proximal end and distally thereof to mergence with apex color. (iv) Adaxial surface—Commonly light olive (near 10 Y 5/4) (10 Y 5/6), moderate yellow green (near 2.5 GY 5/4) (2.5 GY 5/6) (2.5 GY 6/6) and/or dark greenish yellow (10 Y 6/6) at proximal end and merging distally thereof with apex color. (7) Pinnae: (a) General—Sessile, foliaceous with primary rachilla bearing a compact arrangement of pinnules. (b) Arrangement—Predominately alternate with occasional opposite arrangement at proximal end of rachis. (c) Shape—(i) General: Lanceolate. (ii) Pinna tips. Acute to acuminate. (iii) Pinna bases: Generally acute. (d) Size—(i) Length (maximum): Majority on fronds are usually between 6 cm. and 20 cm. (ii) Width (maximum): Usually less than 6.2 cm. for longest pinna on rachis. (e) Primary Rachilla—(i) General: Herbaceous, fleshy and flexible during early maturity and hardening with age. (ii) Texture: Short cespitose hairs sparsely concentrated on ventral (lower) surface, moderately concentrated on dorsal (upper) surface and moderate to heavy concentration at secondary rachilla insertions. (iii) Orientation: Acute angle between axis of primary rachilla and rachis portion distally of rachilla insertion and rotated so that pinnules projecting basally of rachis usually overlap distally projecting pinnules of adjacent, more proximally located, pinna. (iv) Shape: Generally oval in cross section with major axis generally normal to general plane of primary and secondary rachilla and with a longitudinally extending depression or groove in the dorsal surface. (v) Spacing: Usually between 5 mm. and 15 mm. between primary rachilla. (vi) Size: (*a*) Length—Usually between 6 cm. and 20 cm. on majority of mature fronds. (*b*) Diameter—Usually between 0.3 mm. and 1.2 mm. intermediate insertion and apex on mature fronds. (vii) Color: Commonly light yellow green (2.5 GY 8/6), moderate yellow green (2.5 GY 7/6) (5 GY 6/4) (5 GY 6/6) (5 GY 7/4) (5 GY 7/6) (near 7.5 GY 6/4) (near 7.5 GY 6/6) and/or strong yellow green (near 2.5 GY 7/8) (5 GY 7/8). (f) Pinnules—(i) General: Simple, sessile and fleshy. (ii) Texture: Generally glabrous, upper epidermal surface with some pinnules exhibiting sparse pubescence, and pubescent lower epidermal surface that diminishes with maturity and age. (iii) Arrangement: Usually alternate with some opposite tendencies at insertion of primary rachilla. (iv) Shape: Generally lanceolate. (v) Margins: Irregular and variable with crenate, double crenate, and some dentate tendencies, alone and in conjunction with pinnately lobed and/or parted margins. (vi) Size: (*a*) Length—Usually between 8 mm. and 62 mm. (*b*) Width (maximum)—Usually less than 10 mm. (*c*) Thickness: usually less than 0.3 mm. (vii) Color: Both epidermal surfaces are commonly moderate yellow green (near 2.5 GY 5/4) (2.5 GY 5/6) (5 GY 5/4) (5 GY 5/6) (5 GY 6/4) (5 GY 6/6) (near 5 GY 7/6) (7.5 GY 5/4) (7.5 GY 5/6), moderate olive green (5 GY 4/4) (7.5 GY 4/4) (7.5 GY 4/6), and/or dark yellowish green (10 GY 4/4) (near 10 GY 4/6). (viii) Sori: None. (ix) Secondary rachilla: (*a*) General—Herbaceous, flexible and fleshy. (*b*) Texture—Generally glabrous to very slightly pubescent. (*c*) Orientation—Usually ranging from perpendicular to primary rachilla to an acute angle between primary rachilla portion distally of secondary rachilla insertion.

(*d*) Spacing—Usually between 0.2 mm. and 6.5 mm. (*e*) Shape—Elongated. (*f*) Size—[a] Length: Majority of mature pinnule are usually between 8 mm. and 62 mm. [b] Diameter: usually less than 1.0 mm.

V. Gametophyte: None.

The above description is based on observations made during the months of June and July of well fertilized plants about eight (8) months old (from initial propagation) and which were grown under 85% shaded nursery conditions in the Fort Lauderdale, Fla. area and wherein temperatures range approximately from 60–85° during the winter months and approximately from 75–95° during the summer months.

The following is a general description of a plant specimen of the new variety which was propagated and grown under the above nursery conditions, the description being taken in the month of July.

I. General:

(a) Plant age—8 months.

(b) Soil—Sterile peat housed in 10 inch (industrial classification) plastic container.

II. Stems:

(a) Stolons—(1) Number: 19 primary. (2) Diameter: 1.3 mm. (av.). (3) Branches per primary stolon: 6.3 (av.). (4) Color: Includes light greenish yellow (near 10 Y 8/6), moderate greenish yellow (7.5 Y 7/6), strong greenish yellow (near 10 Y 7/8), brilliant greenish yellow (near 10 Y 8/6), light yellow green (2.5 GY 8/6), moderate yellow green (2.5 GY 7/6) (5 GY 6/6) (5 GY 7/6), and strong yellow green (2.5 GY 7/8) (5 GY 6/8) (5 GY 7/8).

III. Fronds:

(a) General: (1) Number of mature fronds—12. (2) Number of immature fronds—3.

(b) Size: (1) Length (including stipe)—52 cm., 67.6 cm., 81.2 cm., 79.7 cm., 56.3 cm., 60.1 cm., 68.7 cm., 82.3 cm., 80.1 cm., 66.7 cm., 48.0 cm., and 48.3 cm. for respective fronds. (2) Width (maximum)—24.6 cm., 25.8 cm., 38.1 cm., 37.4 cm., 26.3 cm., 28.2 cm., 29.4 cm., 37.7 cm., 37.1 cm., 29.8 cm., 22.8 cm., and 23.7 cm. for respective fronds.

(c) Stiple: (1) Length—8.6 (av.). (2) Diameter—2.6 (av.). (3) Color—(a) Apexes: Include moderate yellow green (2.5 GY 6/6) (5 GY 5/6) and strong yellow green (2.5 GY 6/8) (2.5 GY 7/8). (b) Abaxial surface: Includes dark red (2.5 R 3/4) (5 R 3/43, moderate reddish brown (7.5 R 3/4) (near 10 R 3/4). (c) Adaxial surface: Includes light olive (10 Y 5/6) and moderate yellow green (2.5 GY 5/6) (2.5 GY 6/6).

(d) Pinna: Primary rachilla—(1) Length: Majority between 8 and 18 cm. (2) Diameter: 8.1 mm. (av.) between insertion and apex on mature fronds. (3) Color: Includes moderate yellow green (2.5 GY 7/6) (5 GY 7/4) (5 GY 7/6) and strong yellow green (5 GY 7/8). (4) Pinnules: (i) Length—32.6 mm. (av.). (ii) Width—6.1 mm. (av.). (iii) Thickness—0.23 mm. (av.). (iv) Color—Includes moderate olive green (5 GY 4/4) (7.5 GY 4/4) (7.5 GY 4/6), dark yelowish green (10 Y 4/4), and moderate yellow green (2.5 GY 5/6) (5 GY 5/4) (5 GY 5/6) (5 GY 6/6).

I claim:

1. The new and distinct plant variety of the fern family substantially as herein described and characterized by a growth habit which provides specimens that have robust appearing, compound, bipinnate fronds that grow in a compact rosette arrangement with a notable absence of sori, and that in comparison to the fronds of the *Nephrolepis exaltata* "Curly Boston" variety are faster maturing, generally longer and wider appearing at maturity, and provided with a rachis having an abaxial surface color at its proximal end that extends further distally on the rachis than that of the "Curly Boston" variety and is dominated by red and/or reddish brown hues.

No references cited.

ROBERT E. BAGWILL, Primary Examiner